United States Patent
Chen et al.

(10) Patent No.: US 9,855,306 B2
(45) Date of Patent: Jan. 2, 2018

(54) ***PORTULACA OLERACEA* L. EXTRACT FEED ADDITIVE AND PREPARATION METHOD THEREOF**

(71) Applicant: Shanghai Zhao Xiang Biological Technology Co., LTD, Shanghai (CN)

(72) Inventors: Jiaming Chen, Shanghai (CN); Xuefeng Chen, Shanghai (CN); Ling Lu, Shanghai (CN); Ting Shu, Shanghai (CN); Zili Chen, Shanghai (CN); Ziqiang Chen, Shanghai (CN); Danrong Zheng, Shanghai (CN); Shunjie Huang, Shanghai (CN)

(73) Assignee: Shanghai Zhao Xiang Biological Technology Co., LTD, Shanghai (CN)

( * ) Notice: Subject to any disclaimer, the term of this patent is extended or adjusted under 35 U.S.C. 154(b) by 287 days.

(21) Appl. No.: 14/687,810

(22) Filed: Apr. 15, 2015

(65) Prior Publication Data
US 2015/0297657 A1 Oct. 22, 2015

(30) Foreign Application Priority Data
Apr. 16, 2014 (CN) .......................... 2014 1 0153227

(51) Int. Cl.
*A61K 36/185* (2006.01)
*A23K 20/10* (2016.01)

(52) U.S. Cl.
CPC ............ *A61K 36/185* (2013.01); *A23K 20/10* (2016.05); *A61K 2236/00* (2013.01)

(58) Field of Classification Search
None
See application file for complete search history.

(56) References Cited

FOREIGN PATENT DOCUMENTS

| CN | 102552525 A | * | 7/2012 |
|---|---|---|---|
| CN | 102875687 A | * | 1/2013 |

* cited by examiner

*Primary Examiner* — Susan Hoffman

(57) ABSTRACT

A *Portulaca oleracea* L. extract feed additive and a preparation method thereof are provided. The *Portulaca oleracea* L. extract feed additive takes a *Portulaca oleracea* L. extract and a carrier as raw materials. The *Portulaca oleracea* L. extract is prepared by the ultrasonic auxiliary water extraction. The preparation method of the present invention has less raw material waste, high activity component content in the extract and acquisition rate of the extractum, which facilitates improving the effect efficiency and reducing production cost. The *Portulaca oleracea* L. extract feed additive as a natural plant feed additive is capable of improving the animal's metabolism, increasing the animal's relative weight gain, improving the animal's survival rate, reducing the disease incidence of various diarrhea symptoms, decreasing the animal's stress response and increasing the animal productivity.

19 Claims, No Drawings

PORTULACA OLERACEA L. EXTRACT FEED ADDITIVE AND PREPARATION METHOD THEREOF

CROSS REFERENCE OF RELATED APPLICATION

The present invention claims priority under 35 U.S.C. 119(a-d) to CN 201410153227.X, filed Apr. 16, 2014.

BACKGROUND OF THE PRESENT INVENTION

Field of Invention

The present invention relates to a Chinese herbal medicine feed field, and more particularly to a *Portulaca oleracea* L. extract feed additive and a preparation method thereof.

Description of Related Arts

With the continuous development of China breeding industry, diseases of various culture animals have become a prominent problem which restricts the development of China breeding industry. As far as commonly seen infectious diseases are concerned, the variety thereof is complex, such as bacterial diseases, parasitic diseases and viral diseases. Similarly, local farmers are deeply puzzled by various diseases which spread through respiratory tract and digestive tract. Respiratory tract and digestive tract diseases increasingly threaten pig industry in China, which reaches the extent that must be solved. Currently, vaccination and medical treatment are mainly used in breeding industry to avoid the above mentioned diseases. Although medical treatment is more effective and is mainly used, its side effects, such as producing and enlarging resistance to drugs, and producing environmental pollution, are very obvious.

Plant extract is one of main feed antibiotic substitutes and is a natural substance. It is capable of promoting animal growth, improving animal constitution, increasing metabolism, improving production performance, resisting stress, preventing diseases, etc., which is in the leading level in China. Foreign countries have very strict requirements for food, and especially, European Union which is internationally the earliest, largest and most strict region where feed antibiotic is strictly prohibited. Feed additives are successfully prohibited in European Union, the reason is that: besides excellent feeding and management supporting facilities, there is a very important physical measurement that feed antibiotic is replaced by the plant extract (Chinese herbal medicine). The Chinese herbal medicine plays a very important role in successfully prohibiting feed antibiotic.

*Portulaca oleracea* L. is a Portulacaceae, Genus *Portulaca* plant. According to ancient medical records, such as the Northern and Southern Dynasties of China "Supplementary Records of Famous Physicians", Tang Dynasty of China "Dietetic material medica" and Ming Dynasty of China "Compendium of Materia Medica", *Portulaca oleracea* L. is capable of clearing away heat and toxic materials, scattering blood detumescence, and avoiding dysentery. Fresh *Portulaca oleracea* L. is mixed with water to treat acute enteritis, dysentery and diarrhea in Chinese folk. Researches show that the juice of *Portulaca oleracea* L. is capable of obviously restricting *staphylococcus aureus* and *escherichia coli*, reducing blood fat and eliminating inflammation. However, related researches on the value and function of *Portulaca oleracea* L. as fodder has not been reported.

SUMMARY OF THE PRESENT INVENTION

An object of the present invention is to overcome the shortcomings of the above prior art and provide a *Portulaca oleracea* L. extract feed additive and a preparation method thereof. While extracting a traditional Chinese medicine plant, the most critical aspect is to select the solvent, set the steps, optimize the temperature and set ratios of components. It is found through a large number of experimental studies that the present invention achieves a most efficient, simple and practical method of preparing a *Portulaca oleracea* L. extract without any pollutions, and extracts farthest active ingredients from the *Portulaca oleracea* L. extract for preparing a natural plant feed additive to improve the animal's metabolism, increase the animal's relative weight gain, improve the animal's survival rate, reduce the disease incidence of various diarrhea symptoms, decrease the animal's stress response and increase the animal productivity.

The above object is achieved by the technical solution as follows.

On the one hand, the present invention relates to a *Portulaca oleracea* L. extract feed additive comprising a *Portulaca oleracea* L. extract and a carrier, wherein the *Portulaca oleracea* L. extract is prepared by an ultrasonic auxiliary water extraction.

Preferably, a weight ratio of the *Portulaca oleracea* L. extract and the carrier is 1:(2-6). More preferably, the weight ratio is 1:(5-6).

Preferably, the carrier is a mixture of attapulgite, maltodextrin and orange peel powder with a weight ratio of 1:(2-3):(0.5-1).

On the other hand, the present invention also relates to a method of preparing the above *Portulaca oleracea* L. extract feed additive, comprising steps of:

(1) pretreating and smashing *Portulaca oleracea* L., adding ethanol solution to immerse for 5-6 h; removing to an ultrasonic extractor for ultrasonically extracting at room temperature for 30-45 min; filtering after the extraction for obtaining a filtrate and a first solid residue; vacuum evaporating for removing ethanol in the filtrate to obtain a first extracting solution;

(2) adding eight times an amount of water into the first solid residue, boiling for 4-6 h at a steam pressure of 0.4-0.7 MPa, filtering to obtain a second extracting solution and a second solid residue;

(3) adding six times an amount of water into the second solid residue, boiling for 1-3 h at a steam pressure of 1.4-1.6 MPa, filtering to obtain a third extracting solution and a third solid residue;

(4) mixing the first extracting solution, the second extracting solution and the third extracting solution, concentrating for obtaining a first extractum; spraying and drying to obtain a *Portulaca oleracea* L. extract dry powder; and (5) evenly mixing the *Portulaca oleracea* L. extract dry powder with a carrier to obtain the *Portulaca oleracea* L. extract feed additive.

Preferably, the step of pretreating and smashing *Portulaca oleracea* L. comprises naturally drying and impurity removing stems and leafs of the *Portulaca oleracea* L., drying for 6 h at 60° C., smashing, and sieving through a sieve with an aperture of 0.8-1.2 mm. If a particle is undersize, the *Portulaca oleracea* L. powder is easy to float on the feed liquid, so that the extraction effect is affected; if the particle is oversize, the extraction efficiency is reduced more.

Preferably, an amount of the added ethanol solution is 15-20 ml ethanol solution per gram *Portulaca oleracea* L., wherein a concentration of ethanol in the ethanol solution is 75 wt %-85 wt %. The concentration and amount of the ethanol solution have larger effects on the acquisition rate of the extractum. When the amount of the ethanol solution is increased to a certain degree (wherein a concentration of ethanol solution is 85 wt %, an amount thereof is that 20 ml ethanol solution is added per gram *Portulaca oleracea* L.), increasing the amount of the ethanol solution has no obvious effects on the acquisition rate of the extractum. After overall consideration of cost and effect, 15-20 ml ethanol solution is added per gram *Portulaca oleracea* L., wherein when a concentration of ethanol in the ethanol solution is 75 wt %-85 wt %, the technology is best.

Preferably, while ultrasonically extracting, an ultrasonic frequency is 110-125 KHz.

Preferably, while ultrasonically extracting, moisture is distilled simultaneously for collecting a distillate. The distillate is *Portulaca oleracea* L. volatile oil containing linalool, norepinephrine, linolenic acid lipid, 3,7,11,15-tetramethyl-2-sixteen enol, yak-diol, and seventeen carbon alkane. According to the present invention, the distillate is sold as a secondary product and is capable of mixing with the first extraction solution, the second extraction solution and the third extraction solution, and then concentrating for subsequent preparation.

Preferably, in the step (2), acetic acid is added to adjust a PH value of solution to 6.0, and in the step (3), saturated NaOH is added to adjust a PH value of solution to 8.0.

Preferably, before spraying and drying, the step (4) further comprises steps of: eluting the first extractum with silica gel column chromatography gradient which takes petroleum ether/ethyl acetate as an eluent with a ratio of petroleum ether/ethyl acetate=3:1, 2:1 and 1:1, and an eluting time of 15 min, combining eluting solutions, concentrating for obtaining a second extractum, spraying and drying the second extractum to obtain the *Portulaca oleracea* L. extract dry powder.

Compared with the prior art, the present invention has beneficial effects as follows.

(1) It is capable of reducing animals' disease incidence and relieving summer-heat.

(2) It is capable of decreasing the occurrence of diarrhea, enhancing the body immunity and promoting growth.

(3) It has strong palatability and is capable of improving feed intake.

(4) It is natural and green without any chemical medicines or hormone, no residue, no tolerance and no toxic side effect.

These and other objectives, features, and advantages of the present invention will become apparent from the following detailed description, and the appended claims.

DETAILED DESCRIPTION OF THE PREFERRED EMBODIMENT

The present invention is further explained in detail with the accompanying embodiments.

Example 1

The example 1 relates to a *Portulaca oleracea* L. extract feed additive. A method of preparing the above *Portulaca oleracea* L. extract feed additive comprises steps of:

Step 1: naturally drying and impurity removing stems and leafs of *Portulaca oleracea* L., drying for 6 h at 60° C., smashing, sieving through a sieve with an aperture of 1.2 mm, adding 20 ml, 85 wt % ethanol solution per gram *Portulaca oleracea* L. to immerse for 6 h; removing to an ultrasonic extractor for ultrasonically extracting at room temperature and a frequency of 120 KHz for 40 min; filtering after the extraction for obtaining a filtrate and a first solid residue; vacuum evaporating for removing ethanol in the filtrate to obtain a first extracting solution;

Step 2: adding eight times an amount of water into the first solid residue, boiling for 5 h at a steam pressure of 0.6 MPa, filtering to obtain a second extracting solution and a second solid residue;

Step 3: adding six times an amount of water into the second solid residue, boiling for 2 h at a steam pressure of 1.5 MPa, filtering to obtain a third extracting solution and a third solid residue;

Step 4: mixing the first extracting solution, the second extracting solution and the third extracting solution, concentrating till D (which is a proportion of the mixed solution)=0.6-1.1 for obtaining an extractum; putting the extractum into a spray dryer with an inlet air temperature of 180° C. and an outlet air temperature of 80° C. (which is able to be in a range of 70-90° C.) to obtain a *Portulaca oleracea* L. extract dry powder; and Step 5: evenly mixing the *Portulaca oleracea* L. extract dry powder with a carrier (which is a mixture of attapulgite, maltodextrin and orange peel powder with a weight ratio of 1:2:1) to obtain the *Portulaca oleracea* L. extract feed additive, wherein a weight ratio of the *Portulaca oleracea* L. extract dry powder and the carrier is 1:5.

Comparative Example 1

The comparative example 1 relates to a *Portulaca oleracea* L. extract feed additive. A method of preparing the above *Portulaca oleracea* L. extract feed additive comprises steps of:

Step 1: naturally drying and impurity removing stems and leafs of *Portulaca oleracea* L., drying for 6 h at 60° C., smashing, sieving through a sieve with an aperture of 1.2 mm; adding the sieved *Portulaca oleracea* L. into an alcohol extraction tank, adding eight times an amount of 85 wt % ethanol, boiling for 6 h at a steam pressure of 0.7 MPa, making an ethanol reflux; filtering after firstly extracting ethanol for obtaining a first filtrate and a first filter residue, wherein ethanol is recycled from the first filtrate by a decompression concentration tank till a concentration of the recycled ethanol is smaller than 60%, concentrating the first filtrate to obtain a concentrated solution;

Step 2: adding eight times an amount of 85 wt % ethanol into the first filter residue, boiling for 5 h at a steam pressure of 0.6 MPa, making an ethanol reflux, wherein ethanol is recycled till a concentration of the recycled ethanol is smaller than 60%, filtering to obtain a second filtrate and a second filter residue;

Step 3: adding six times an amount of water into the second filter residue, boiling for 2 h at a steam pressure of 1.5 MPa, filtering to obtain a third filtrate and a third filter residue; discarding the third filter residue;

Step 4: mixing the concentrated solution, the second filtrate and the third filtrate, concentrating till D (which is a proportion of the mixed solution)=0.6-1.1 for obtaining an extractum; putting the extractum into a spray dryer with an inlet air temperature of 180° C. and an outlet air temperature of 80° C. to obtain a *Portulaca oleracea* L. extract dry powder; and Step 5: evenly mixing the *Portulaca oleracea* L. extract dry powder with a carrier (which is a mixture of attapulgite, maltodextrin and orange peel powder with a weight ratio of 1:2:1) to obtain the *Portulaca oleracea* L. extract feed additive, wherein a weight ratio of the *Portulaca oleracea* L. extract dry powder and the carrier is 1:5.

Example 2

An object of the example 2 is to study the effects of a PH value in a step of water extraction after ultrasonically extracting on a ratio of dry extraction and an extraction ratio of active components. The preparation method of the example 2 is as same as that of the example 1, and the differences therebetween are that: in the step (2) of the example 2, respectively add acetic acid to adjust a PH value of solution to 5.5, 6.0 and 6.5, and respectively add saturated NaOH to adjust a PH value of solution to 7.5, 8.0 and 9.0 in the step (3) of the example 2 for forming nine experimental groups, wherein nine experimental groups 2a-2i respectively correspond to nine groups of PH values in step (2) and step (3) which are respectively 5.5, 7.5; 5.5, 8.0; 5.5, 9.0; 6.0, 7.5; 6.0, 8.0; 6.0, 9.0; 6.5, 7.5; 6.5, 8.0; 6.5, 9.0.

Take 100 g *Portulaca oleracea* L. medicinal material to make a comparative experiment on the example 1, the example 2 and the comparative example 1 as follows.

Measure the ratio of dry extraction: respectively mix the first extracting solution, the second extracting solution and the third extracting solution obtained by the above nine experimental groups and the example 1; the concentrated solution, the second filtrate and the third filtrate obtained by the comparative example 1, and concentrate the mixture to be with a volume of 500 ml, take 20 ml concentrated solution to a moisture analyzer for determining moisture, and calculate the ratio of dry extraction of the extract based on a moisture value.

Measurement results are shown in Table 1.

TABLE 1

| | EG 2a | EG 2b | EG 2c | EG 2d | EG 2e | EG 2f | EG 2g | EG 2h | EG 2i | E1 | CE1 |
|---|---|---|---|---|---|---|---|---|---|---|---|
| RODE (%) | 22.1 | 21.5 | 22.3 | 22.8 | 23.0 | 21.7 | 24.5 | 22.0 | 21.2 | 21.8 | 15.9 |

* Note:
Experimental Group is abbreviated as EG, Example 1 is abbreviated as E1, Comparative Example is abbreviated as CE1, and the ratio of dry extraction is abbreviated as RODE.

It can be seen from Table 1 that when acetic acid is added to adjust the PH value of solution to 6.0 in the step (2), and saturated NaOH is added to adjust the PH value of solution to 8.0 in the step (3), the ratio of dry extraction of the extract is best.

Example 3

The example 3 relates to a *Portulaca oleracea* L. extract feed additive, the preparation method thereof is as same as that of the example 1 and the differences therebetween are as follows.

Before spraying drying, following steps further included: eluting the extractum with silica gel column chromatography gradient which takes petroleum ether/ethyl acetate as an eluent with a ratio of petroleum ether/ethyl acetate=10:1; 5:1; 3:1; 2:1; 1:1, 1:5 and an eluting time of 15 min, respectively collecting eluting solution, concentrating for obtaining a new extractum, spraying and drying to obtain the *Portulaca oleracea* L. extract dry powder. Evenly mix the six groups of *Portulaca oleracea* L. extract dry powder with a carrier (which is a mixture of attapulgite, maltodextrin and orange peel powder with a weight ratio of 1:2:1) to obtain the *Portulaca oleracea* L. extract feed additives which are respectively recorded as Experimental group 3a, Experimental group 3b, Experimental group 3c, Experimental group 3d, Experimental group 3e and Experimental group 3f, wherein a weight ratio of the *Portulaca oleracea* L. extract dry powder and the carrier is 1:5.

Example 4

An object of the example 4 is to study the effects of various carriers on the *Portulaca oleracea* L. extract feed additive. The preparation method thereof is as same as that of example 1 and the differences therebetween are as follows. The carriers are respectively selected from attapulgite, maltodextrin, and a mixture of attapulgite, maltodextrin and orange peel powder with a weight ratio of 1:3:0.5, and a mixture of attapulgite, maltodextrin and pine needle powder with a weight ratio of 1:2:1, which are respectively recorded as Experimental group 4a, Experimental group 4b, Experimental group 4c, and Experimental group 4d.

Comparatively experiment on the examples 1, 3, 4 and the comparative example 1 at the experimental place of Yuanheng animal Chinese medicine research center, Shanghai of China. The experimental animals are three-breed growing-finishing pigs bred in the late and fed with mixing materials, wherein 650 g *Portulaca oleracea* L. extract feed additives are added per ton fodder. No *Portulaca oleracea* L. extract feed additive is added to the comparative group. Feed for 100 days.

Experimental results are shown in Table 2.

TABLE 2

| Test indexes | | Relative weight rate (%) | Rate of survival (%) | Feces inflammation secretion rate (%) | Urine abnormal rate (%) | Respiratory system abnormal rate (%) |
|---|---|---|---|---|---|---|
| Comparative Group | | 100 | 95.0 | 42.5 | 15 | 40 |
| Comparative Example 1 | | 105.5 | 97.0 | 15.5 | 5.3 | 15.8 |
| Example | 1 | 116.9 | 100 | 5 | 0 | 5 |
| | 2h | 121.5 | 100 | 3.5 | 0 | 4.5 |
| | 3a | 111.3 | 98.5 | 5.5 | 2 | 4.0 |
| | 3b | 116.5 | 100 | 3.5 | 1.5 | 5.2 |
| | 3c | 125.2 | 100 | 1.5 | 0 | 3.0 |
| | 3d | 130.5 | 100 | 2.0 | 0 | 3.2 |
| | 3e | 128.4 | 100 | 1.5 | 0 | 2.5 |
| | 3f | 117.2 | 98.5 | 4.5 | 0 | 4.7 |
| | 4a | 112.8 | 99 | 6.5 | 2.5 | 6.3 |
| | 4b | 113.0 | 99 | 6.0 | 3 | 7.2 |
| | 4c | 117.0 | 100 | 4.5 | 0 | 5.5 |
| | 4d | 110.5 | 98 | 8.5 | 6.0 | 9.5 |

It can be seen from Table 2 by comparing the examples 1, 4a, 4b, 4c, and 4d that: the mixture of attapulgite, maltodextrin and orange peel powder with a weight ratio of 1:(2-3):(0.5-1) as the carrier is capable of playing a synergic role in the *Portulaca oleracea* L. extract and reducing the feces inflammation secretion rate, the urine abnormal rate and the respiratory system abnormal rate of pigs. It can be found by comparing experimental groups in the example 3 that: when the eluent with the ratio of petroleum ether/ethyl acetate=3:1; 2:1; 1:1 is used, the eluted component is capable of significantly reducing the feces inflammation secretion rate, the urine abnormal rate and the respiratory system abnormal rate of pigs and improving rate of survival and relative weight gain. All in all, the *Portulaca oleracea* L. extract feed additive of the present invention is capable of improving the animal's metabolism, increasing the animal's relative weight gain, improving the animal's survival rate, reducing the disease incidence of various diarrhea symptoms, decreasing the animal's stress response and increasing the animal productivity.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A *Portulaca oleracea* L. extract feed additive, comprising a *Portulaca oleracea* L. extract and a carrier, wherein the *Portulaca oleracea* L. extract is prepared by a method comprising steps of:
   (1) pretreating and smashing *Portulaca oleracea* L., immersing for 5-6 h after adding ethanol solution; ultrasonically extracting at room temperature for 30-45 min through an ultrasonic extractor; and then filtering and obtaining a filtrate and a first solid residue; and then vacuum evaporating for removing ethanol in the filtrate and finally obtaining a first extracting solution;
   (2) adding eight times an amount of water into the first solid residue, boiling for 4-6 h at a steam pressure of 0.4-0.7 MPa, and then filtering and finally obtaining a second extracting solution and a second solid residue;
   (3) adding six times an amount of water into the second solid residue, boiling for 1-3 h at a steam pressure of 1.4-1.6 MPa, and then filtering and finally obtaining a third extracting solution and a third solid residue; and
   (4) mixing the first extracting solution, the second extracting solution and the third extracting solution, and then concentrating and obtaining a first extractum; and then spraying and drying and finally obtaining the *Portulaca oleracea* L. extract.

2. The *Portulaca oleracea* L. extract feed additive, as recited in claim 1, wherein a weight ratio of the *Portulaca oleracea* L. extract and the carrier is 1:5, and the carrier is a mixture of attapulgite, maltodextrin and orange peel powder with a weight ratio of 1:(2-3):(0.5-1).

3. A method of preparing a *Portulaca oleracea* L. extract feed additive, comprising steps of:
   (1) pretreating and smashing *Portulaca oleracea* L., immersing for 5-6 h after adding ethanol solution; ultrasonically extracting at room temperature for 30-45 min through an ultrasonic extractor; and then filtering and obtaining a filtrate and a first solid residue; and then vacuum evaporating for removing ethanol in the filtrate and finally obtaining a first extracting solution;
   (2) adding eight times an amount of water into the first solid residue, boiling for 4-6 h at a steam pressure of 0.4-0.7 MPa, and then filtering to obtain a second extracting solution and a second solid residue;
   (3) adding six times an amount of water into the second solid residue, boiling for 1-3 h at a steam pressure of 1.4-1.6 MPa, and then filtering to obtain a third extracting solution and a third solid residue;
   (4) mixing the first extracting solution, the second extracting solution and the third extracting solution, and then concentrating and obtaining a first extractum; and then spraying and drying to obtain a *Portulaca oleracea* L. extract dry powder; and
   (5) evenly mixing the *Portulaca oleracea* L. extract dry powder with a carrier to obtain the *Portulaca oleracea* L. extract feed additive.

4. The method, as recited in claim 3, wherein the step of pretreating and smashing *Portulaca oleracea* L. comprises naturally drying and removing stems and leafs of the *Portulaca oleracea* L., drying for 6 h at 60° C., smashing, and sieving through a sieve with an aperture of 0.8-1.2 mm.

5. The method, as recited in claim 3, wherein an amount of the added ethanol solution is 15-20 ml ethanol solution per gram *Portulaca oleracea* L., wherein a concentration of ethanol in the ethanol solution is 75 wt %-85 wt %.

6. The method, as recited in claim 4, wherein an amount of the added ethanol solution is 15-20 ml ethanol solution per gram *Portulaca oleracea* L., wherein a concentration of ethanol in the ethanol solution is 75 wt %-85 wt %.

7. The method, as recited in claim 3, wherein while ultrasonically extracting, an ultrasonic frequency is 110-125 KHz.

8. The method, as recited in claim 6, wherein while ultrasonically extracting, an ultrasonic frequency is 110-125 KHz.

9. The method, as recited in claim 3, wherein while ultrasonically extracting, moisture is distilled simultaneously for collecting a distillate.

10. The method, as recited in claim 8, wherein while ultrasonically extracting, moisture is distilled simultaneously for collecting a distillate.

11. The method, as recited in claim 3, wherein in the step (2), acetic acid is added to adjust a PH value of solution to 6.0, and in the step (3), saturated NaOH is added to adjust a PH value of solution to 8.0.

12. The method, as recited in claim 10, wherein in the step (2), acetic acid is added to adjust a PH value of solution to 6.0, and in the step (3), saturated NaOH is added to adjust a PH value of solution to 8.0.

13. The method, as recited in claim 3, wherein before spraying and drying, the step (4) further comprising steps of: eluting the first extractum with silica gel column chromatography gradient which takes petroleum ether/ethyl acetate as an eluent and eluting with petroleum ether/ethyl acetate at a ratio of 3:1, 2:1 and 1:1, and an eluting time of 15 min, combining eluting solutions, concentrating for obtaining a second extractum, spraying and drying the second extractum to obtain the *Portulaca oleracea* L. extract dry powder.

14. The method, as recited in claim 12, wherein before spraying and drying, the step (4) further comprising steps of: eluting the first extractum with silica gel column chromatography gradient which takes petroleum ether/ethyl acetate as an eluent and eluting with petroleum ether/ethyl acetate at a ratio of 3:1, 2:1 and 1:1, and an eluting time of 15 min, combining eluting solutions, concentrating for obtaining a second extractum, spraying and drying the second extractum to obtain the *Portulaca oleracea* L. extract dry powder.

15. The method, as recited in claim 3, wherein a weight ratio of the *Portulaca oleracea* L. extract dry power and the carrier is 1:(2-6).

16. The method, as recited in claim 13, wherein a weight ratio of the *Portulaca oleracea* L. extract dry power and the carrier is 1:(2-6).

17. The method, as recited in claim 14, wherein a weight ratio of the *Portulaca oleracea* L. extract dry power and the carrier is 1:(2-6).

18. The method, as recited in claim 3, wherein the carrier is a mixture of attapulgite, maltodextrin and orange peel powder with a weight ratio of 1:(2-3):(0.5-1).

19. The method, as recited in claim 17, wherein the carrier is a mixture of attapulgite, maltodextrin, and orange peel powder with a weight ratio of 1:(2-3):(0.5-1).

* * * * *